United States Patent [19]

Johnson et al.

[11] Patent Number: 5,958,788
[45] Date of Patent: *Sep. 28, 1999

[54] LUMINOL TAGGED POLYMERS FOR TREATMENT OF INDUSTRIAL SYSTEMS

[75] Inventors: Brian S. Johnson, Warrenville; William J. Ward, Glen Ellyn, both of Ill.

[73] Assignee: Nalco Chemical Company, Naperville, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/864,656

[22] Filed: May 28, 1997

[51] Int. Cl.$^6$ .................................................... G01N 21/76
[52] U.S. Cl. ............................. 436/172; 436/55; 436/56; 436/86; 436/164; 436/166; 436/800; 422/3; 422/62
[58] Field of Search .................................. 436/55, 56, 86, 436/164, 166, 172, 800; 422/3, 62

[56] References Cited

U.S. PATENT DOCUMENTS

| | | | |
|---|---|---|---|
| 4,152,200 | 5/1979 | Coscia et al. | 162/168.3 |
| 4,166,105 | 8/1979 | Hirschfeld | 436/536 |
| 4,217,262 | 8/1980 | Coscia et al. | 524/801 |
| 4,783,314 | 11/1988 | Hoots et al. | 422/3 |
| 4,788,142 | 11/1988 | Hosaka et al. | 435/29 |
| 5,003,050 | 3/1991 | Kiel et al. | 534/573 |
| 5,128,419 | 7/1992 | Fong et al. | 525/351 |
| 5,171,450 | 12/1992 | Hoots | 210/701 |
| 5,216,086 | 6/1993 | Fong et al. | 525/351 |
| 5,260,386 | 11/1993 | Fong et al. | 525/340 |
| 5,413,719 | 5/1995 | Sivakumar et al. | 210/708 |
| 5,435,969 | 7/1995 | Hoots et al. | 422/14 |
| 5,645,799 | 7/1997 | Shah et al. | 422/62 |
| 5,705,394 | 1/1998 | Ananthasubramanian et al. | 436/55 |

FOREIGN PATENT DOCUMENTS

| | | |
|---|---|---|
| 58137759 | 8/1983 | Japan . |
| 05034330 | 2/1993 | Japan . |
| WO 92/13272 | 8/1992 | WIPO . |

*Primary Examiner*—Maureen M. Wallenhorst
*Attorney, Agent, or Firm*—Hill & Simpson

[57] ABSTRACT

A polymer tagged with luminol is provided which enables the fluorescent or chemiluminescent detection of the tagged polymer at low concentrations. The chromophore may be covalently bonded to the polymer backbone without sacrificing the chromophore's fluorescent or chemiluminescent properties. The present invention has been found useful in the treatment and monitoring of industrial waters.

3 Claims, 3 Drawing Sheets

LUMINOL TAGGED POLYMERS FOR TREATMENT OF INDUSTRIAL SYSTEMS

BACKGROUND OF THE INVENTION

The present invention relates generally to the treatment and monitoring of industrial systems and, more specifically, to the treatment and monitoring of industrial systems using luminol-tagged polymers in combination with fluorescent or chemiluminescent detection techniques.

Polymeric coagulants are added to industrial water systems and waste water systems as monitoring agents because technological advances have enabled those skilled in the art to feasibly monitor the residual level of such polymeric coagulant additives. Knowledge of the fate of polymeric coagulants in industrial water and waste water systems enables operators to monitor the residual content of the polymeric coagulants and therefore the residual content of other compositions in the water.

Further, by monitoring the residual level of polymeric coagulants in waste water, operators are able to better control the addition of such coagulants. Specifically, the knowledge that the concentration of a polymeric coagulant at a downstream location is rather high will enable the operator to reduce the addition of the polymeric coagulant at an upstream location. As a result, coagulant dosage can be automated. Still further, a knowledge of the fate of coagulant in a system assists in the diagnosing of treatment difficulties and, potentially, a diagnosing of treatment difficulties before the difficulties reduce in non-conformance treated water.

The typical approach to monitoring the level of water soluble polymer coagulants in a system has been to blend fluorescent dyes in small amounts and to use the fluorescence of the mixture to determine the concentration of the polymer in the system. While this approach has been relatively successful, it has limitations. Specifically, fluorescent dyes can become associated with other components of the system, such as sample particulates. Accordingly, a subsequent fluorescent detection of the dye may not necessarily provide evidence of the location or detection of the polymeric coagulant.

Accordingly, there is a need for a polymer that can be modified so that the dye is chemically incorporated into or otherwise attached to the polymer. Because the dye and polymer would be physically attached, detection of the dye would necessarily result in a detection of the polymer. Of course, it would be economically important that the dye be readily detectable at low concentrations. A highly fluorescent or chemiluminescent dye would therefore be desirable. Further, for widespread applicability, a water soluble polymer is required. Accordingly, there is a need for a dye-modified water soluble polymer in which the dye is highly fluorescent or chemiluminescent and which could be readily detected in the part per million (ppm) or part per billion (ppb) range using existing fluorescent detection techniques and/or chemiluminescent techniques.

REFERENCE TO RELATED APPLICATION

U.S. Pat. No. 5,705,394 issued on Jan. 6, 1998, which, like this application, is assigned to Nalco Chemical Company, the concept of tagging epichlorohydrin-dimethylamine polymers with a fluorescent moiety is disclosed. This application constitutes an improvement over the invention disclosed in U.S. Pat. No. 5,705,394 in that it discloses the use of water soluble polymers tagged with luminol.

SUMMARY OF THE INVENTION

The present invention satisfies the aforenoted needs by providing a composition that is capable of being detected in a solution by chemiluminescent techniques as well as fluorescent techniques. More specifically, the present invention provides a polymer tagged with luminol that can be detected even at very low concentrations in a solution utilizing either chemiluminescent or fluorescent techniques. The present invention also provides an improved method for detecting the presence of a substance or composition in a solution.

In an embodiment, the present invention provides a composition capable of being detected in a solution by chemiluminescent or fluorescent detection techniques which comprises a polymer tagged with luminol.

In an embodiment, the polymer comprises epichlorohydrin monomer units.

In an embodiment, the polymer is further characterized as being a copolymer comprising epichlorohydrin monomer units and dimethylamine monomer units.

In an embodiment, the polymer is a copolymer comprising epichlorohydrin monomer units and dimethylamine monomer units with luminol covalently bonded between some of the epichlorohydrin monomer units and dimethylamine monomer units, the luminol being present in the copolymer in an amount ranging from about 0.05% to about 2% by weight.

In an embodiment, a tagged portion of the polymer of the present invention has the following formula:

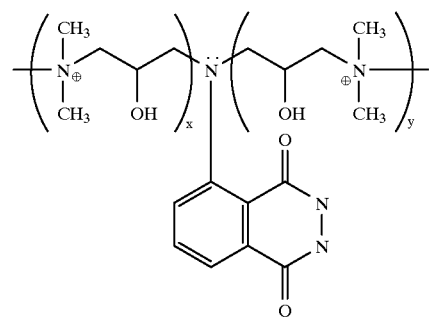

In an embodiment, the present invention provides a composition comprising epichlorohydrin monomer tagged with luminol.

In an embodiment, the present invention provides the composition comprising a luminol tagged monomer.

It is therefore an advantage of the present invention to provide a monomer tagged with a chemiluminescent and/or fluorescent chromophore that can be detected in a solution at low concentrations utilizing conventional chemiluminescent or fluorescent detection techniques.

Another advantage of the present invention is to provide a polymer tagged with a chemiluminescent/fluorescent chromophore such as luminol that can be detected in a solution at low concentrations using conventional chemiluminescent or fluorescent techniques.

Yet another advantage of the present invention is the ability to tag a polymer with luminol during the condensation polymer reaction resulting in luminol covalently bonded to the polymer.

Yet another advantage of the present invention is to provide an improved method of tagging a monomer or a polymer with luminol.

Another advantage of the present invention is to provide an improved method of tagging a monomer or a polymer with luminol.

Another advantage of the present invention is to provide an improved composition for use in dosage control, residuals monitoring, automated particle sizing control, and in the general treatment of industrial waters.

DETAILED DESCRIPTION OF THE PRESENTLY PREFERRED EMBODIMENTS

Figure 1:
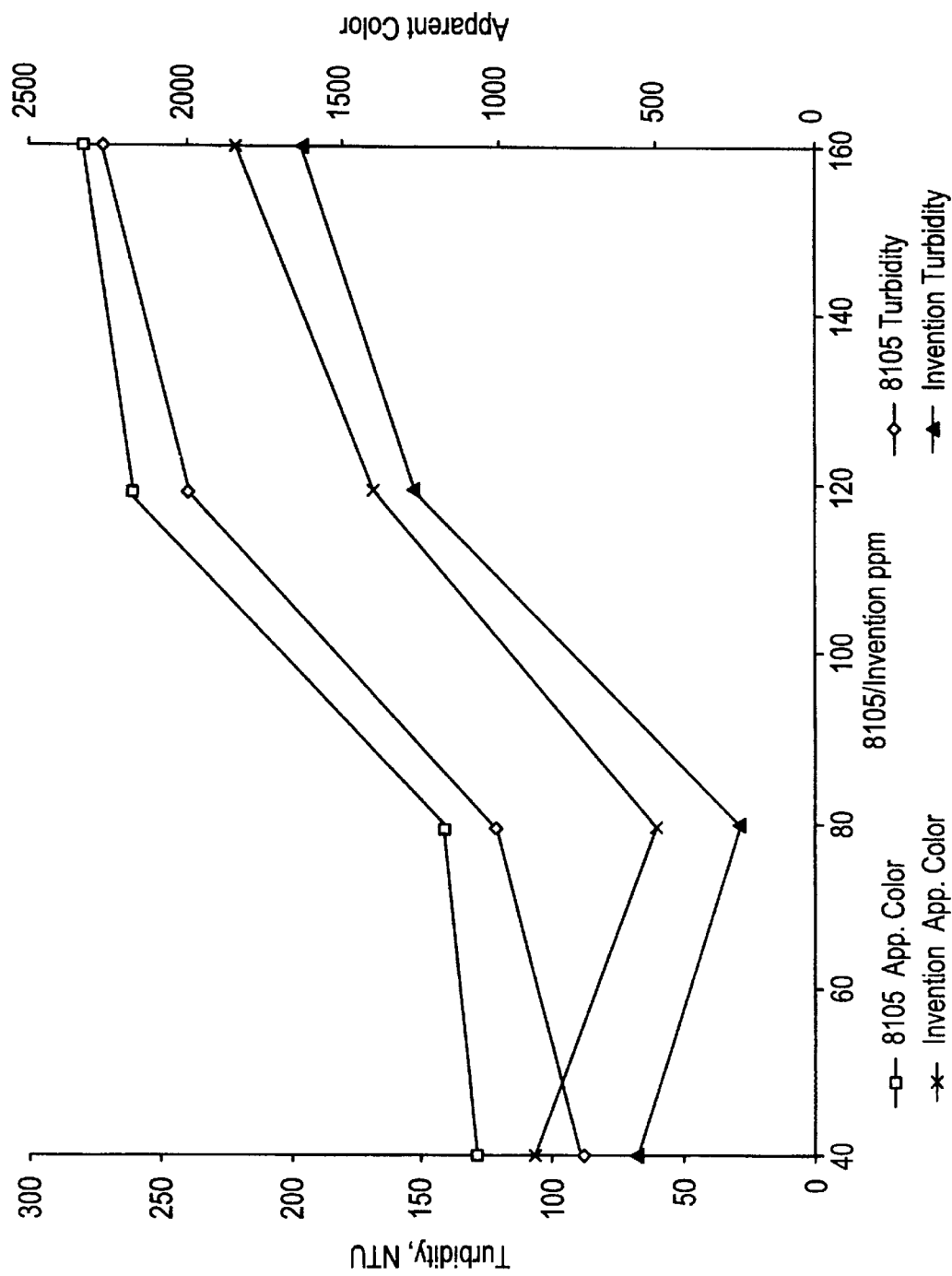
FIG. 1 illustrates, graphically, the ability of a composition prepared in accordance with the present invention to act as a coagulant while being detectable at low dosages.

The present invention provides an improved composition that can be detected at low concentrations using conventional fluorescent or chemiluminescent detection methods. One embodiment of the present invention is luminol tagged epichlorohydrin-dimethylamine polymer.

Luminol is a chemiluminescent species with its structure being shown below:

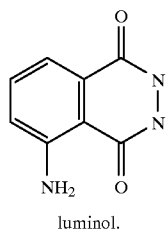

luminol.

The structure of epichlorohydron and dimethylamine are shown below:

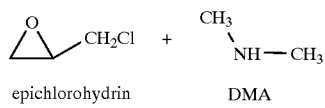

epichlorohydrin     DMA

The structure of a tagged portion of luminol tagged epichlorohydrin-dimethylamine polymer is shown below:

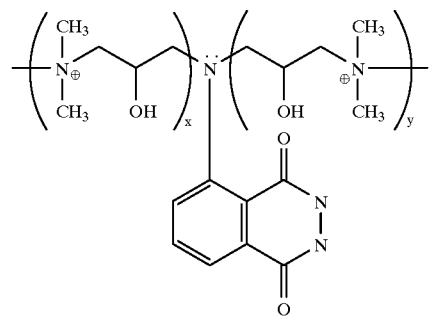

It is also anticipated that in addition to luminol, nile blue and thionine can also be used as chromophores as well. In addition, it is also anticipated that a monomer, such as epichlorohydron can be tagged with a chromophore to provide a composition capable of being detected by fluorescent or chemiluminescent methods at low concentrations in accordance with the present invention.

The invention comprises copolymers of epichlorohydrin-dimethylamine which contains from 0.05%–2% by weight of luminol. It is noted that any condensation polymerization process could incorporate luminol as long as the chromophore's fluorescent properties were retained.

The invention further contemplates using these polymers in water treating applications such as, but not limited to, coagulation. This allows the dosage and residual quantities of the polymers to be controlled and monitored using conventional fluorescence/chemiluminescent detecting equipment even though the polymers are present in the ppb range.

The reaction of luminol, epichlorohydron and dimethylamine to provide a luminol tagged epichlorohydron-dimethylamine polymer. The presumed structure is shown below:

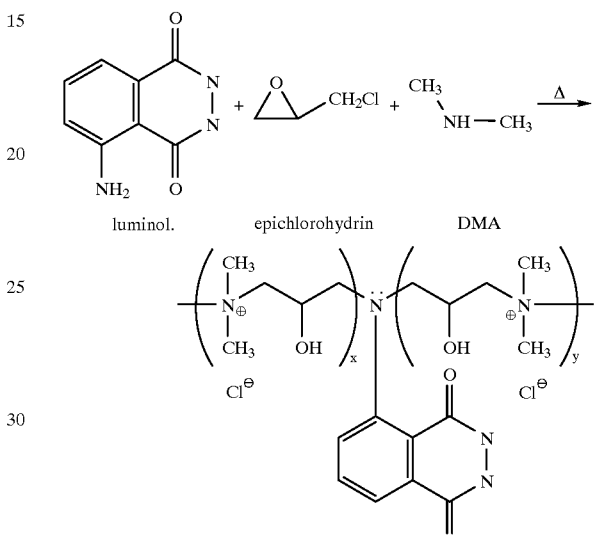

Utilizing the primary aromatic amine group in luminol, the luminol is incorporated into the polymer's backbone. The hydrocarbon linkage is essentially a tertiary amine leaving the ring nitrogens available for fluorescent or chemiluminescent applications. It is also theoretically possible to react epichlorohydrin with luminol and then polymerize into the usual epichlorohydrin/dimethylamine reaction, forming essentially the same tagged polymer.

The luminol and dimethylamine are desirably reacted with the epichlorohydron at 80° C. using general synthetic methods that are known to those skilled in the art. Specifically, the ephichlorohydron polymers modified by luminol may be synthesized using known condensation polymerization techniques. The resulting copolymers may contain from about 0.05% to about 2% by weight of the luminol monomer. Of course, luminol is a monomer and potentially can be incorporated at higher levels. Preferably, the amount of fluorescent monomer is within the range of 0.1% to 1% by weight of the resulting tagged polymer.

A luminol tagged epichlorohydron-dimethylamine monomer prepared in accordance with the present invention has an average molecular weight of 10,000 amu versus 20,000 amu for an unmodified epichlorohydron-dimethylamine polymer. For most water treating applications, such as coagulation, the molecular weight should be less than c.a. 100,000 amu.

When used to treat industrial waters, the dosage of the modified polymers should usually vary from a few parts per million (ppm) up to several hundred ppm depending upon the system being treated and the intrinsic viscosity of the polymer in use. When used as a coagulant, the dosage should typically be between a few ppm up to approximately 100 ppm.

EXAMPLE 1

The following laboratory procedure was used to prepare the embodiment of the present invention comprising luminol tagged epichlorohydron-dimethylamine polymers. To a 300 mL Parr reactor, was added 1.67 g of luminol, 79.67 g of water and 70.70 g of 61.3% dimethylamine in water. After sealing the Parr Reactor, the temperature was increased to 65° C. Then epichlorohydrin was added at roughly 1.5 ml/min until the temperature reached 80° C. Since the reaction is exothermic, the epichlorohydrin addition rate was varied to keep the temperature at approximately 80° C. Once a total of 86.655 g of epichlorohydrin had been added, the reactor temperature was maintained at 80° C. for two hours after which the mixture was then cooled to room temperature.

The following procedures were used to characterize the polymer. Brookfield viscosity was obtained using a #2 spindle at 30 rpm. For two batches of the invention, the Brookfield viscosity varied from 100 cps to 400 cps. Dialysis experiments were performed using a 12,000 to 14,000 amu MW cut-off membrane. Since luminol is not water-soluble, dialysis was performed in methanol. This separates unreacted luminol from the invention. Testing shows that luminol monomers was essentially entirely incorporated at 0.7% by weight of product with at least 99% incorporation of the dye into the polymer being achieved. Total polymer solids of the tagged polyDADMAC was measured at 54.4%.

The composition of the present invention had the following characteristics:

TABLE 1

|  | Tagged Epi-DMA | Epi-DMA |
| --- | --- | --- |
| Appearance: | Clear Yellow | Clear Yellow |
| Brookfield Viscosity: | 100–400 cps | 270 cps |
| Wt. Average MW: | 10,000 | 20,000 |
| Polymer Solids: | 54.4% | 55% |

The composition of the present invention has similar characteristics to untagged epichlorohydrin/dimethylamine polymer. Luminol incorporation was determined analytically.

Activity testing was performed by testing papermill effluent with fresh and aged luminol-epichlorohydrin/dimethylamine copolymer. Coagulation power is unchanged. It was noted that the invention is light sensitive and at room temperature, will darken over a six month period. A portion saved in darkness for the same time period at 4° C. showed only moderate color change.

TEST RESULTS

Paper mill effluent wastewater was used for activity testing. FIG. 1 shows that activity of the tagged polymer versus untagged polymer.
This result proves that chemically tagging epichlorohydrin/dimethylamine shows similar coagulation activity compared to untagged epichlorohydrin/dimethylamine polymer. Activity was determined by effluent turbidity as measured in NTUs (nephrolytic turbidity units).

Figure 2:
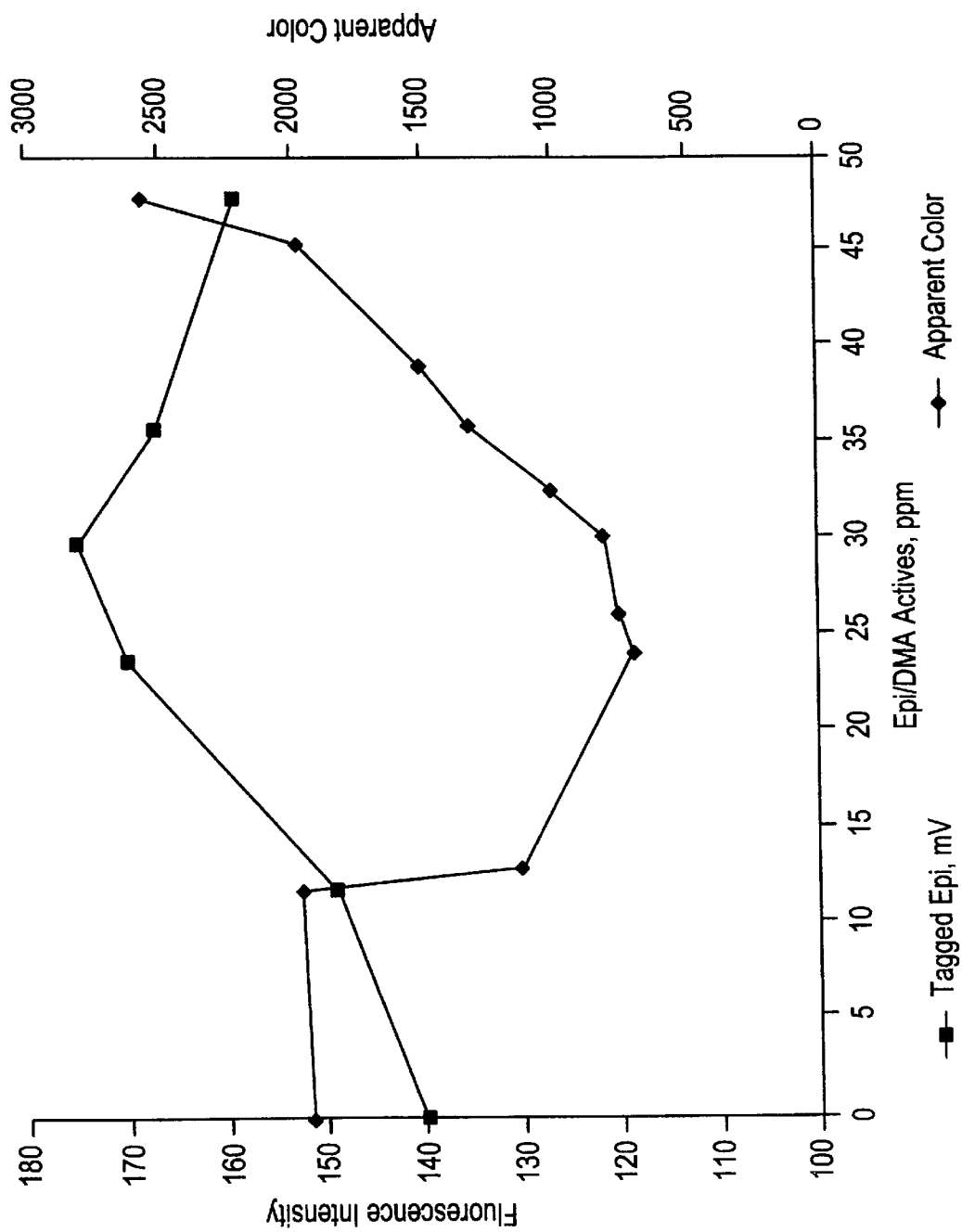
FIG. 2 illustrates, graphically, the ability of a composition prepared in accordance with the present invention to provide fluorescent information over a low dosage range.
Figure 3:
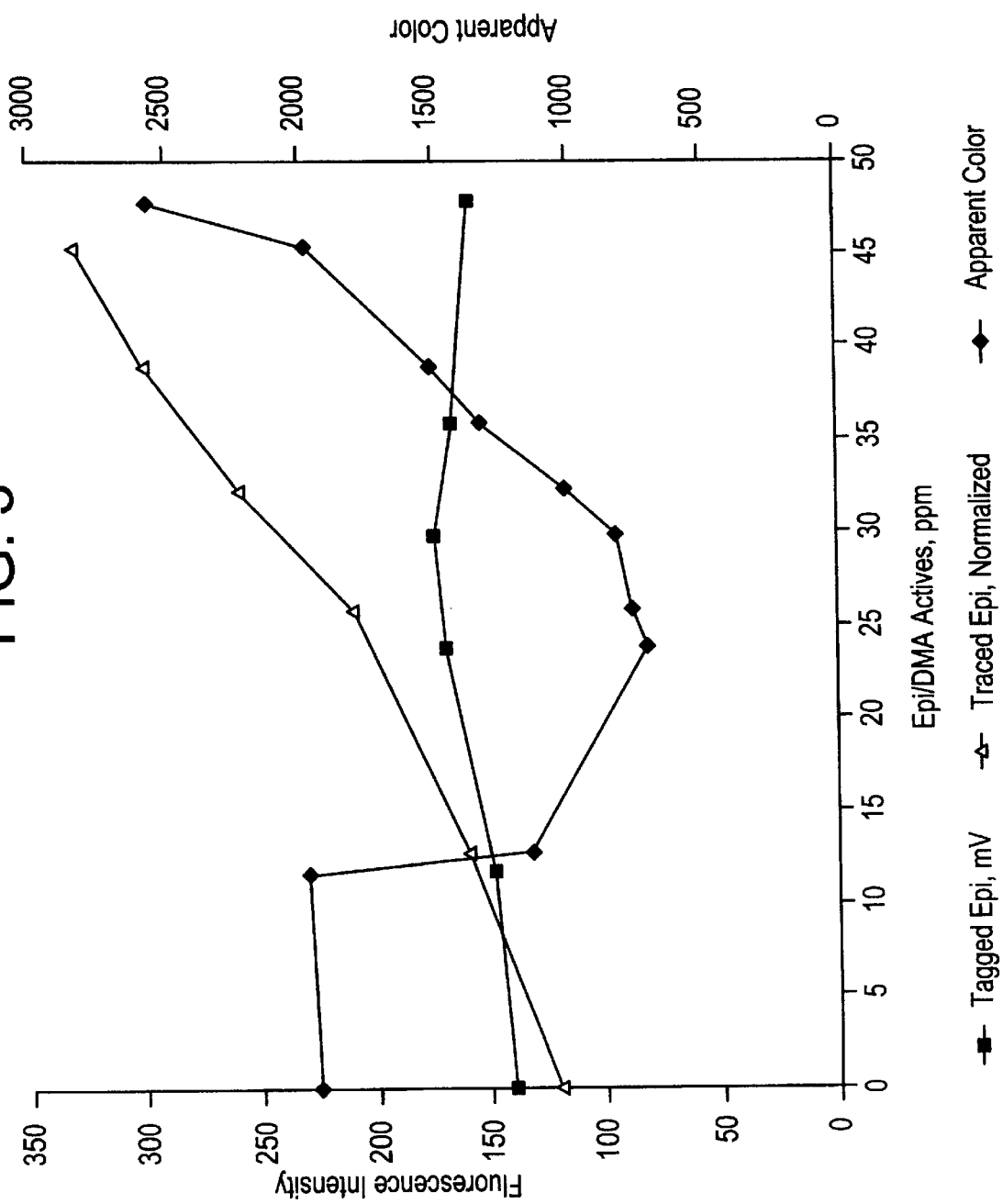
FIG. 3 illustrates, graphically, the correlation of a composition prepared in accordance with the present invention to apparent color removal performance and the non-correlation of a prior art composition to apparent color removal performance.

Further testing of the invention was done to compare performance in TRASAR applications. Paper mill effluent is treated with traced (as opposed to tagged) epichlorohydrin/dimethylamine. Normally, an inverse correlation with apparent color removal is noted. FIG. 2 demonstrates that the invention has the same expected fluorescence residuals with apparent color removal. Occasionally, the traced product shows no correlation; the water in FIGS. 2 and 3 were performed on such water. From FIG. 3, it is illustrated that the invention demonstrates a correlation with apparent color removal while the traced epichlorohydrin/dimethylamine has no correlation. Thus, the invention has a performance enhancement over traced products and advances the state of the art for automated dosage applications.

Accordingly, the present invention provides a tagged polymer that is useful in the treatment of industrial waters. Specifically, the tagged polymers made in accordance with the present invention can be used to monitor treated water residuals, control coagulant addition and be used in the analysis of coagulation mechanisms. By improving the detectability of polymeric coagulants and by improving the ability to control the dosage levels of these coagulants, the present invention helps to minimize the contribution to pollution attributable to polymeric coagulants.

Further, by covalently bonding a chromophore to a polymer, the present invention avoids the shortcomings associated with the prior art method of blending fluorescent dyes with polymeric coagulants which, as discussed above, results in a physical separation or disassociation between the dye and coagulant.

As illustrated in FIGS. 1 and 2, polymers tagged with a chromophore in accordance with the present invention are detectable at low dosage levels. Finally, as illustrated in FIG. 1, the modified or tagged polymer prepared in accordance with the present invention has an activity similar to an unmodified polymer.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that all such changes and modifications be covered by the appended claims.

What is claimed is:

1. A coagulant capable of being detected in a water stream by chemiluminescent or fluorescent detection, the coagulant comprising:
    a copolymer comprising epichlorohydrin monomer units and dimethylamine monomer units, a portion of the copolymer being tagged by covalent bond to luminol, the luminol being present in an amount ranging from about 0.05% to about 2% by weight,
    wherein the tagged portion of the copolmer has the formula:

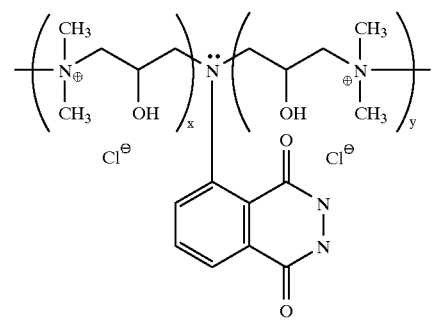

2. A method of detecting the presence of a coagulant in a system at a downstream location after the coagulant has been added to the system at an upstream location, the method comprising the following steps:
    adding the coagulant to the system at the upstream location, the coagulant comprising a composition capable of being detected in a solution by chemiluminescent or fluorescent detection, the coagulant comprising a copolymer comprising epichlorohydrin monomer units and dimethylamine monomer units, a portion of the copolymer being tagged by covalent bond to luminol, the luminol being present in an amount ranging from about 0.5% to about 2% by weight, wherein the tagged portion of the copolymer has the formula:

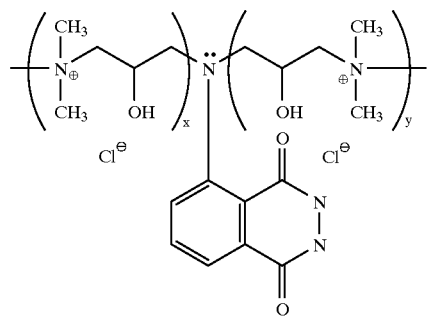

and detecting the presence of the coagulant with chemiluminescent or fluorescent detection at the downstream location.

3. A copolymer comprising epichlorohydrin monomer units and dimethylamine monomer units, a portion of the copolymer being tagged by covalent bond to luminol, the covalent bond being located between one of said epichlorohydrin monomer units and one of said dimethylamine monomer units, the luminol being present in an amount ranging from 0.05% to 2% by weight, wherein the tagged portion of the copolmer has the formula:

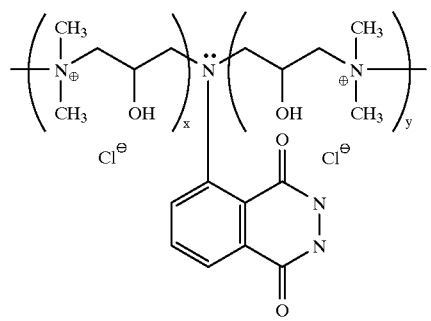

* * * * *